(12) United States Patent
Suissa et al.

(10) Patent No.: US 11,857,703 B2
(45) Date of Patent: Jan. 2, 2024

(54) FRAGRANCE DELIVERY SYSTEM

(71) Applicant: SCENTYS, Paris (FR)

(72) Inventors: David Suissa, Fontenay-sous-Bois (FR); Laurent Martin, Saint-Melaine-sur-Aubance (FR)

(73) Assignee: SCENTYS, Paris (FR)

( * ) Notice: Subject to any disclaimer, the term of this patent is extended or adjusted under 35 U.S.C. 154(b) by 648 days.

(21) Appl. No.: 16/643,135

(22) PCT Filed: Aug. 17, 2018

(86) PCT No.: PCT/FR2018/052073
§ 371 (c)(1),
(2) Date: Feb. 28, 2020

(87) PCT Pub. No.: WO2019/043319
PCT Pub. Date: Mar. 7, 2019

(65) Prior Publication Data
US 2020/0390925 A1 Dec. 17, 2020

(30) Foreign Application Priority Data
Aug. 30, 2017 (FR) ....................................... 1757976

(51) Int. Cl.
*A61L 9/12* (2006.01)
*A61L 9/04* (2006.01)

(52) U.S. Cl.
CPC ................. *A61L 9/12* (2013.01); *A61L 9/042* (2013.01); *A61L 2209/133* (2013.01); *A61L 2209/15* (2013.01)

(58) Field of Classification Search
CPC ...... A61L 9/12; A61L 9/042; A61L 2209/133; A61L 2209/15

USPC .......................... 239/33, 55, 57, 34; 422/123
See application file for complete search history.

(56) References Cited

U.S. PATENT DOCUMENTS

| 9,248,212 | B2 | 2/2016 | Suissa | |
| 2013/0341424 | A1* | 12/2013 | Brandenburg | A61L 9/12 239/57 |
| 2015/0217017 | A1* | 8/2015 | Venisti | B60H 3/0028 239/55 |

(Continued)

FOREIGN PATENT DOCUMENTS

| EP | 1932545 A1 | 6/2008 |
| WO | 2013021114 A1 | 2/2013 |

OTHER PUBLICATIONS

International Search Report for PCT/FR2018/052073 dated Oct. 29, 2018.

*Primary Examiner* — Steven J Ganey
(74) *Attorney, Agent, or Firm* — Bachman & LaPointe, P.C.

(57) ABSTRACT

A fragrance delivery system comprising at least one cartridge containing solid elements loaded by adsorption of an olfactory composition and opened by a grid having holes, the cross-section of which is smaller than the cross-section of the solid elements, wherein the solid elements are made of a polymer ensuring a natural delivery of the fragrances for a period of 6 to 18 months, and in that the cartridge is mounted on a cartridge holder holding the cartridge and connected to a mounting base on a fixed portion by an unstable linkage capable of ensuring an oscillating movement of the cartridge holder around a reference position.

9 Claims, 2 Drawing Sheets

(56) References Cited

U.S. PATENT DOCUMENTS

2017/0106114 A1  4/2017  Frankenbach

* cited by examiner

FRAGRANCE DELIVERY SYSTEM

BACKGROUND

The present invention concerns the field of delivery of fragrances using solid holders in which are adsorbed odorous molecules which are released into the atmosphere by spontaneous delivery or by means of an air flow. It concerns in particular the field of delivery of fragrances in the passenger compartment of a vehicle (a car, a railway, a plane, a boat, . . . ) using interchangeable capsules comprising substrate elements in which a fragrance is adsorbed.

More specifically, it concerns passive delivery systems which offer the advantage of requiring no energy input. The fragrance is put in the open air and takes advantage of the different air movements to disperse in the atmosphere to be perfumed.

STATE OF THE ART

A European patent application EP1932545 describing a container for delivering volatile substances impregnated with solid or semi-solid materials is known in the state of the art, characterized in that said container is filled with a load of granules of said materials and is provided with openings of shape and size allowing the release of the volatile substance but not of the granules.

There is also a U.S. patent application US2017/106114 describing a fluid-permeable pouch enclosing a chamber, the pouch comprising a bond that at least partially defines the chamber; a plurality of particles contained within the chamber, the particles comprising a fragrance; wherein the pouch comprises a loop or an opening sized to fit a garment hanger.

DRAWBACKS OF THE PRIOR ART

The solutions described in the prior art provide for the storage of the odorous molecules in a carrier material such as a porous solid or a gelatine allowing release by evaporation. The fragrance molecules are small molecules with a strong tendency to diffuse through a large number of carrier materials, both porous and gelatine. The drivers of this delivery are volatility and the split between the inner phase and the outer phase. Diffusion losses limit the stability of these systems in products.

The solutions proposed in the prior art therefore have a short life span, typically a few days after removal of their sealed packaging.

The spraying of the fragrance is done in a constant way, whether the holder is at rest or is animated by an oscillating movement.

The swinging of the container simply produces a movement of the air mass where this evaporation takes place, in order to widen the perception area of the evaporated product. At rest, evaporation continues unchanged, the reduced air flow will simply lead to a higher concentration inside the container rather than delivery into a larger volume. It creates an olfactory cloud on the surface of the substrate, the constituents of which are entrained by natural convection.

As a result, the life of the cartridge is short: it corresponds to the time needed for the fragrance to evaporate, i.e., a few days. To compensate for this rapid ageing, the volume of fragrance could certainly be increased, but the constant delivery of the fragrance would not be controlled and could be uncomfortable due to the intensity and volume of the evaporated fragrance.

SUMMARY

The invention aims to remedy the disadvantages of the various solutions of the prior art by proposing a delivery system requiring no electrical power, and making it possible to accelerate the delivery of olfactory substances in relation to the purely static delivery speed, while nevertheless preserving a significant life span, and greater than that observed in solutions providing for a forced air flow through the cartridge.

The objective of this innovation is to create a device allowing the efficient delivery of fragrance in modest volumes (a few $m^3$) using only mechanical energy.

The invention, in its broadest sense, relates in to a fragrance delivery system according to claim 1, taken alone and/or in combination with the characteristics of one or more of the dependent claims.

BRIEF DESCRIPTION OF THE DRAWINGS

The invention will be better understood upon reading the following description, with reference to the attached drawings corresponding to non-exhaustive exemplary embodiments, where.

DETAILED DESCRIPTION

Figure 1:
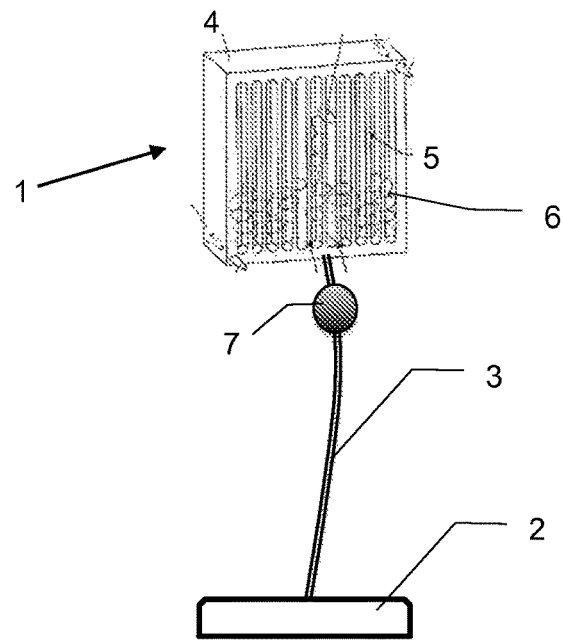
FIG. 1 illustrates a first exemplary embodiment
Figure 2:
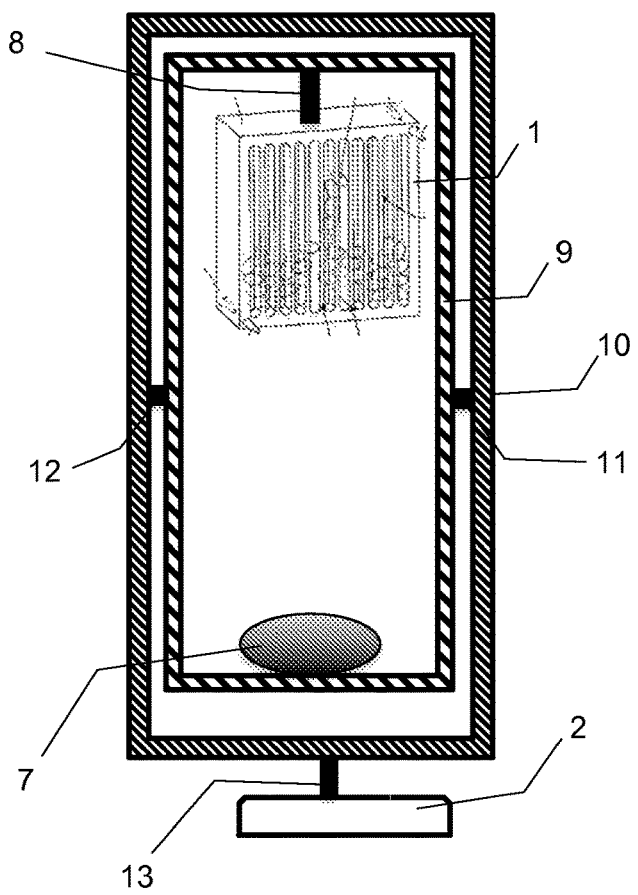
FIG. 2 illustrates a second exemplary embodiment
Figure 3:
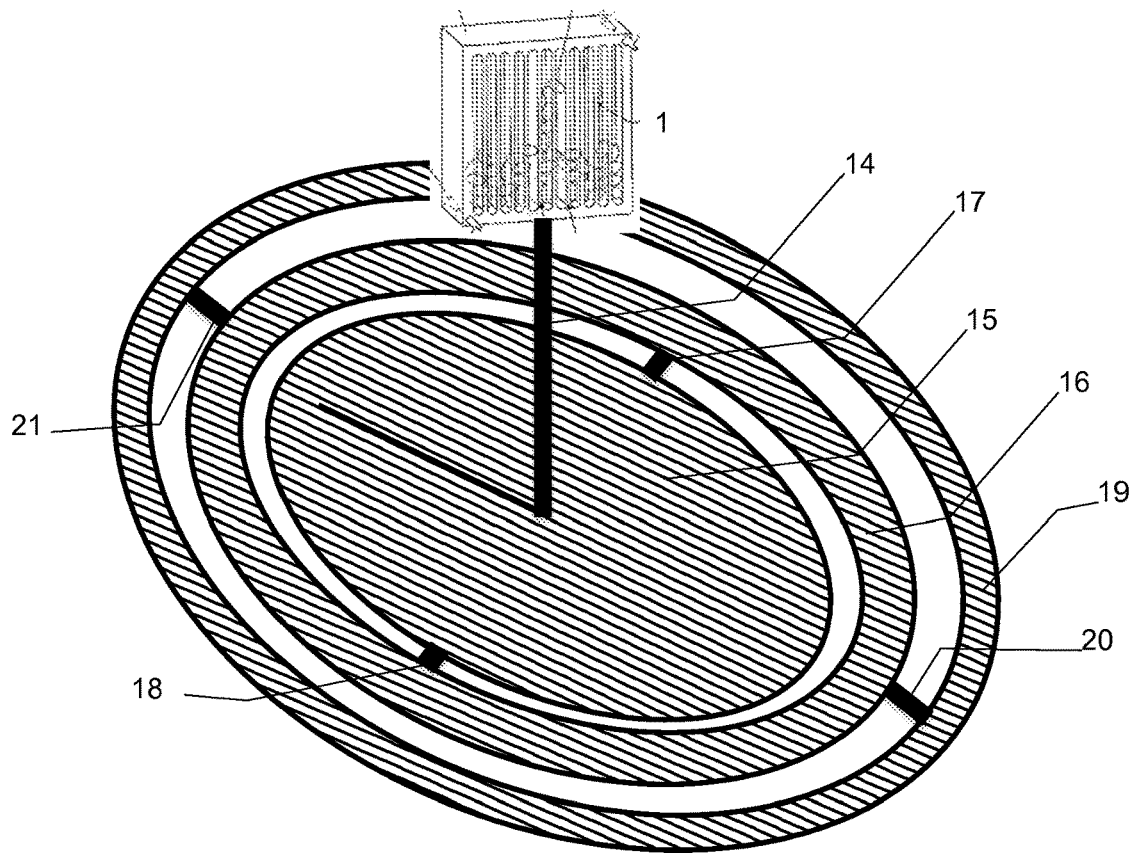
FIG. 3 illustrates a third exemplary embodiment
Figure 4:
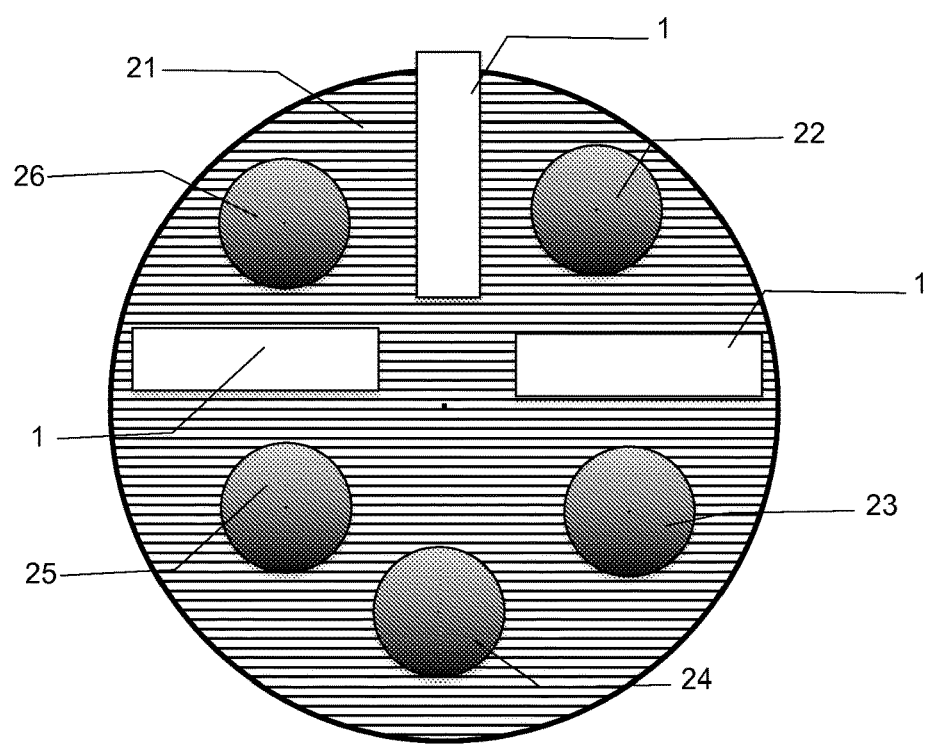
FIG. 4 illustrates a fourth exemplary embodiment.

The solution according to the invention consists in using a fully mechanical energy system for creating a delivery quality of a level similar to electrical devices, but using no external electrical energy source, and fixing the olfactory molecules in a polymer-type substrate.

Fixing of the Olfactory Molecules to the Substrate

The substrate elements are solid. They are made at least in part of a polymer material. Polymers include elastomers, for example a bi-polymer of the polyamide and polyether block amide type. Depending on the used polymer material and the fragrance, the beads naturally deliver the fragrance molecules for 6 to 18 months only in a hardly perceptible way. An example of such a material is Pebax® (trade name).

As they are, the substrate elements spontaneously diffuse small quantities of the fragrance molecules they contain by natural evaporation, or more particularly by a phenomenon of desorption.

On the other hand, when the substrate is subjected to airflow, mechanical interactions significantly increase the rate of release of olfactory molecules by up to 500 times.

The substrate elements 6 may take the form of spheroids, rhombohedral or rectangular parallelepipeds, or prismatoids. In a preferred embodiment, the substrate elements are spheroid beads of polymer material and the fragrance molecules are adsorbed throughout the volume of each bead.

As an example, beads made of polymer material each have, before adsorption of the fragrance, a smaller dimension equal to 3 mm and a larger dimension equal to 4 mm, and, after adsorption of the fragrance, a smaller dimension equal to 4 mm and a larger dimension equal to 6 mm. The weight of fragrance adsorbed in each bead corresponds approximately to the weight of a bead before the fragrance is adsorbed.

The fragrance is encapsulated in polymer beads with fairly strong electrostatic bonds between the molecules making up the fragrance and the polymer beads. Without forced ventilation, the movement of the air does not have enough force to tear off the fragrance molecules and the electrostatic bond prevails. In this configuration, the delivery of fragrance requires about 18 months between the moment when the fragrance capsule is placed in the open air while being completely full of fragrance and the moment when all the available fragrance has been delivered; the delivery is linear way over time. A fragrance capsule containing an average of 2 g of fragrance concentrate means that the amount of fragrance released in a day is: $3.7 \times 10^{-3}$ g/day, i.e., $1.5 \times 10^{-4}$ g/hr.

The polymer beads used are a bi-component polymer comprising apolar and polar portions which allows a relatively strong electrostatic interaction with the different molecules composing the fragrance concentrate which are themselves either polar or apolar. It should also be noted that even when temperature is high (for example in a car passenger compartment, a train or a plane cockpit left in direct sunlight), the quantity of fragrance released is very low: this means that the passenger compartment is not perfumed too strongly when the car is at rest, even in the heat.

In forced ventilation, the kinetic energy brought by the movement of the air is sufficient to tear off the fragrance molecules and in this context, the entire fragrance concentrate is delivered into the air in approximately 24 hrs. The quantity of fragrance released into the air is thus of the order of 2 g/day, i.e. 0.08 g/hr.

By way of comparison, a person who uses 100 ml eau de toilette containing 10% fragrance concentrate by spraying 3 times on him/her, will have put 0.06 g of concentrate on him/her (a 100 ml bottle allows on average 500 sprays), i.e., a quantity of fragrance equivalent to that released by the capsule.

Thus at rest, the olfactory intensity released into the air is about 1000 times less than that released by a person who wears a fragrance, and the olfactory intensity in forced ventilation will be of the same order of magnitude as a person wearing a fragrance.

The general principle implemented by the systems according to the invention consists in using the kinetic energy of a mobile base supported by an unstable linkage, which can take different configurations:

- a flexible rod connecting a cartridge holder containing one or more cartridge(s) to a mounting base fixed to a solid surface, for example the dashboard or ceiling of a vehicle such as a car or a train. During acceleration and deceleration of the vehicle both along the longitudinal and transverse axis (during changes of direction) or vertically (passing over uneven surfaces of a motor vehicle or turbulence for an aircraft), the cartridge holder is subjected to oscillating movements about an equilibrium position.
- A pivot about which the cartridge holder containing one or more cartridge(s) is hinged.

This pivot can be horizontal, with the cartridge holder suspended to allow a swinging movement around an equilibrium position.

This pivot can be vertical, with the cartridge holder rotating freely to allow a swinging movement around an equilibrium position. For the purposes of this patent, "oscillating movement" shall also be mean a rotation of several revolutions around the pivot. The movement will be favoured by the presence of an unbalance on the holder.

The oscillating movements of the cartridge holder cause the cartridge to move relative to the surrounding air, which promotes the controlled release of odour substances.

The cartridge is preferably supported—and not suspended—by the linkage element to the mounting holder, and is therefore placed above the holder.

This configuration provides more "nervousness" to the device, which enters into oscillation as soon as the cartridge is subjected to a movement, resulting for example from the instability of the flexible rod and an acceleration transmitted to the holder.

The movement of the cartridge amplifies the flexible deformation of the rod, unlike a solution where the cartridge is suspended from a flexible linkage where the movement will tend to compensate for the amplitude of the oscillating movement.

Mechanical recovery, for the operation of the device, usually results in intermittent operation. This intermittent mode of operation prevents users from getting used to the odours released and losing the perception of these fragrances. Intermittence allows to regularly reactivate the perception of the odour according to the movements and action of the device. This inconsistency, beyond imposing an irregular operation, rather proposes an experience linked to the activity of the product.

The principle of the solutions presented as non-limiting examples is based on the use of a dry fragrance capsule, as described in patent WO2013021114. This solution ensures that the invention operates safely and conveniently for the user.

In particular, the invention aims to promote the extraction of the fragrance by setting the fragrance capsule in motion instead of the generation of the air flow by a third element, such as a fan.

From a technical point of view, the performance of the delivery is linked to the agitation of the air molecules around the fragrance beads contained in the capsule. The airflow and air pressure around the beads promote desorption of the fragrance from the beads, and the airflow improves the distribution of the fragrance in the air.

Description of a First Embodiment

According to this first exemplary embodiment, the delivery system consists of a cartridge 1, a base 2 and a flexible rod 3.

The cartridge 1 consists of a shell 4 the main faces of which are formed by grids 5. This shell contains solid beads 6 made of a substrate material capable of allowing the penetration or fixation of fragrance molecules at least at their periphery.

This cartridge 1 is fixed to a flexible rod 3, for example a steel piano wire, the other end of which is fixed to a base 2 having for example on its lower surface a suction cup for fixing to a surface such as a vehicle dashboard.

Optionally, the rod 3 is provided with a counterweight 7 on its upper portion. The counterweight is set in motion by all external movements such as vehicle movements and vibrations and/or manual agitation. The flexibility of the rod, its length and the mass of the counterweight determine the quality of the delivery. For example in cars, good results have been obtained with a 0.8 to 1.5 mm thick steel rod, about 10 cm long and a weight of about 50 to 80 g.

Description of a Second Embodiment

In this second embodiment, the cartridge 1 is supported by a vertical pivot 8 fixed on a first oscillating frame 9. This first oscillating frame 9 is positioned inside a second frame 10 via two horizontal axes 11,12. The two frames 9, 10 together form a cardan joint, which is pivotably mounted to the base 2 by means of a vertical pivot 13.

The first frame 9 optionally has a counterweight 7 so that the pivot axis 8 of the pendulum is always perpendicular to the direction of acceleration. Thus, regardless of the direction of acceleration variations, the pivot disc will align and the pendulum will be able to pivot freely on its axis.

Description of a Third Embodiment

According to this third variant, the cartridge 1 is mounted on a disc 15 by means of a rod 14, which can optionally be elastic or rigid. This disc 15 is pivotally mounted with respect to a first frame 16 by means of two pivots 17, 18 oriented in a first direction. This frame is itself pivotally mounted with respect to a second frame 19 by means of two pivots 20, 21 oriented perpendicularly to the first direction.

Description of a Fourth Embodiment

According to this other variant, the cartridge 1 is supported by a flywheel consisting of a disc plate 21, e.g., a metal flywheel with a large mass is rotated manually by the user. Guided in rotation by elements with low coefficients of friction, once the maximum speed has been reached, the inertia will allow the rotating mass to maintain its movement for a long time.

The cartridges 1 are positioned radially in a direction normal to the axis of rotation, so as to correctly take up the relative wind created by the opposition of air to the rotational movement. In order to function properly, this device must have a high 'Rotational Mass/(Capsule Mass*Friction)' ratio, so that it can rotate long enough at the desired speed.

The assembly is pivoted on a fixed base with a ball bearing system and is equipped with a counterweight to add significant unbalance. One or more capsule(s) fixed on the periphery of the disc plate is/are thus animated by the change of orientation of the device. This device has proved effective on the dashboard of a vehicle, but seems to be suitable for integration into a vehicle with regular speed and direction variations such as a bus, a train, a tram or a metro.

Optionally, the platform 21 is equipped with weights 22 to 26, in an unbalanced manner to help set it in motion by the vehicle accelerations transmitted through the base.

The invention claimed is:

1. A fragrance delivery system comprising at least one cartridge containing solid elements loaded by adsorption of an olfactory composition and opened by a grid having holes, the cross-section of which is smaller than the cross-section of the solid elements, wherein said solid elements are made of a bi-component polymer comprising apolar and polar portions; and
    a cartridge holder supporting the at least one cartridge in a position above and connected to a mounting base; the mounting base configured to be fixed;
    wherein said cartridge holder is configured as an unstable linkage capable of ensuring an oscillating movement of said at least one cartridge around a reference position.

2. The fragrance delivery system according to claim 1, wherein said cartridge holder comprises a flexible rod.

3. The fragrance delivery system according to claim 1, wherein said cartridge holder comprises a vertical pivot fixed on a first oscillating frame, the first oscillating frame positioned inside a second frame via two horizontal axes, the first oscillating frame and the second frame together form a cardan joint, mounted pivotal to the mounting base by a vertical pivot.

4. The fragrance delivery system according to claim 1, wherein said cartridge holder comprises a disc with a rod connected to said disc, the rod being configured to attach to said at least one cartridge;
    the disc being pivotally mounted with respect to a first frame by two first frame pivots oriented in a first direction; the first frame being pivotally mounted with respect to a second frame by two second frame pivots oriented perpendicularly to the first direction.

5. A fragrance delivery system comprising at least one cartridge containing solid elements loaded by adsorption of an olfactory composition and opened by a grid having holes, the cross-section of which is smaller than the cross-section of the solid elements, wherein said solid elements are made of a bi-component polymer comprising apolar and polar portions; and
    a flywheel supporting the at least one cartridge, said flywheel including a disc plate guided about an axis of rotation by a bearing system connected on a fixed base.

6. The fragrance delivery system according to claim 5, wherein the flywheel is equipped with a counterweight to add unbalance.

7. The fragrance delivery system according to claim 5, wherein the at least one cartridge is positioned radially in a direction normal to the axis of rotation, so as to take up a relative wind created by an opposition of air to a rotational movement of the flywheel.

8. The fragrance delivery system according to claim 5, wherein the at least on cartridge is fixed on the periphery of the disc plate.

9. The fragrance delivery system according to claim 5, wherein the disc plate is equipped with weights configured in an unbalanced manner, wherein said weights are configured to set the disc plate in motion responsive to a vehicle acceleration transmitted through the fixed base.

* * * * *